United States Patent
Huijgen et al.

(10) Patent No.: US 10,578,980 B2
(45) Date of Patent: Mar. 3, 2020

(54) METHOD OF DETERMINING A POSITION OF A FEATURE

(71) Applicant: ASML NETHERLANDS B.V., Veldhoven (NL)

(72) Inventors: Ralph Timotheus Huijgen, Hillsboro, CA (US); Marc Jurian Kea, Morgan Hill, CA (US); Marcel Theodorus Maria Van Kessel, Maastricht (NL); Masashi Ishibashi, Eindhoven (NL); Chi-Hsiang Fan, San Jose, CA (US); Hakki Ergün Cekli, Eindhoven (NL); Youping Zhang, Cupertino, CA (US); Maurits Van Der Schaar, Eindhoven (NL); Liping Ren, San Jose, CA (US)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/465,161

(22) PCT Filed: Nov. 23, 2017

(86) PCT No.: PCT/EP2017/080190
§ 371 (c)(1),
(2) Date: May 30, 2019

(87) PCT Pub. No.: WO2018/114206
PCT Pub. Date: Jun. 28, 2018

(65) Prior Publication Data
US 2019/0339211 A1  Nov. 7, 2019

(30) Foreign Application Priority Data

Dec. 23, 2016  (EP) .................................... 16206732

(51) Int. Cl.
| | | |
|---|---|---|
| G03B 27/32 | (2006.01) | |
| G03F 7/20 | (2006.01) | |
| G01N 21/956 | (2006.01) | |
| G03F 9/00 | (2006.01) | |

(52) U.S. Cl.
CPC ....... *G03F 7/70633* (2013.01); *G01N 21/956* (2013.01); *G03F 7/705* (2013.01);
(Continued)

(58) Field of Classification Search
CPC .......... G01N 21/956; G01N 21/95607; G01N 21/95615; G01N 2021/95615;
(Continued)

(56) References Cited

U.S. PATENT DOCUMENTS

| | | |
|---|---|---|
| 6,104,471 A | 8/2000 | Morioka et al. |
| 9,134,256 B2 | 9/2015 | Smilde et al. |

(Continued)

FOREIGN PATENT DOCUMENTS

| | | |
|---|---|---|
| CN | 105759570 | 7/2016 |
| EP | 0794465 | 9/1997 |

(Continued)

OTHER PUBLICATIONS

Taiwanese Office Action issued in corresponding Taiwanese Patent Application No. 108106071, dated Jul. 11, 2019.
(Continued)

*Primary Examiner* — Christina A Riddle
(74) *Attorney, Agent, or Firm* — Pillsbury Winthrop Shaw Pittman LLP

(57) ABSTRACT

A method, system and program for determining a position of a feature referenced to a substrate. The method includes measuring a position of the feature, receiving an intended placement of the feature and determining an estimate of a placement error based on knowledge of a relative position of a first reference feature referenced to a first layer on a substrate with respect to a second reference feature referenced to a second layer on a substrate. The updated position may be used to position the layer of the substrate having the feature, or another layer of the substrate, or another layer of another substrate.

20 Claims, 4 Drawing Sheets

(52) U.S. Cl.
CPC ...... *G03F 7/70625* (2013.01); *G03F 7/70691* (2013.01); *G03F 7/70775* (2013.01); *G03F 9/7046* (2013.01); *G03F 9/7092* (2013.01)

(58) Field of Classification Search
CPC .......... G01N 2021/95676; H01L 22/20; H01L 22/12; G03F 7/70625; G03F 7/70633; G03F 7/70691; G03F 7/70483; G03F 7/70491; G03F 7/705–70541; G03F 7/70608; G03F 7/70616; G03F 7/70666; G03F 7/70675; G03F 7/70683; G03F 7/70775; G03F 7/70858; G03F 7/70866; G03F 7/70875; G03F 7/70883; G03F 7/70891; G03F 9/70; G03F 9/7003; G03F 9/7007; G03F 9/7015; G03F 9/7019; G03F 9/7046; G03F 9/7049; G03F 9/7073–7084; G03F 9/7088; G03F 9/7092
USPC ........ 356/138–155, 614–624, 625, 628, 634, 356/635, 636, 388–398, 399–401; 250/492.1, 492.2, 492.22, 493.1; 702/150, 151, 152, 155; 382/144–145, 382/147, 151; 355/30, 52–55, 67, 72–77
See application file for complete search history.

(56) References Cited

U.S. PATENT DOCUMENTS

| | | | |
|---|---|---|---|
| 9,158,209 B2 * | 10/2015 | Chen | G03F 7/70633 |
| 9,530,199 B1 * | 12/2016 | Weinberg | G06T 7/001 |
| 2003/0223630 A1 * | 12/2003 | Adel | G03F 7/705 382/145 |
| 2006/0092419 A1 | 5/2006 | Gui | |
| 2007/0076205 A1 * | 4/2007 | Schulz | G03F 7/70633 356/401 |
| 2014/0065736 A1 | 3/2014 | Amir et al. | |
| 2016/0061589 A1 | 3/2016 | Bhattacharyya et al. | |
| 2016/0266503 A1 | 9/2016 | Van Voorst et al. | |
| 2017/0235233 A1 * | 8/2017 | Lee | G03F 9/7003 355/67 |
| 2017/0363969 A1 | 12/2017 | Hauptmann et al. | |

FOREIGN PATENT DOCUMENTS

| | | |
|---|---|---|
| TW | 201614382 | 4/2016 |
| TW | 201621472 | 6/2016 |
| TW | 201643555 | 12/2016 |
| WO | 2014146906 | 9/2014 |
| WO | 2016096333 | 6/2016 |

OTHER PUBLICATIONS

International Search Report and Written Opinion issued in corresponding PCT Patent Application No. PCT/EP2017/080190, dated Mar. 23, 2018,.

Taiwanese Office Action issued in corresponding Taiwanese Patent Application No. 106144090, dated Aug. 28, 2018.

* cited by examiner

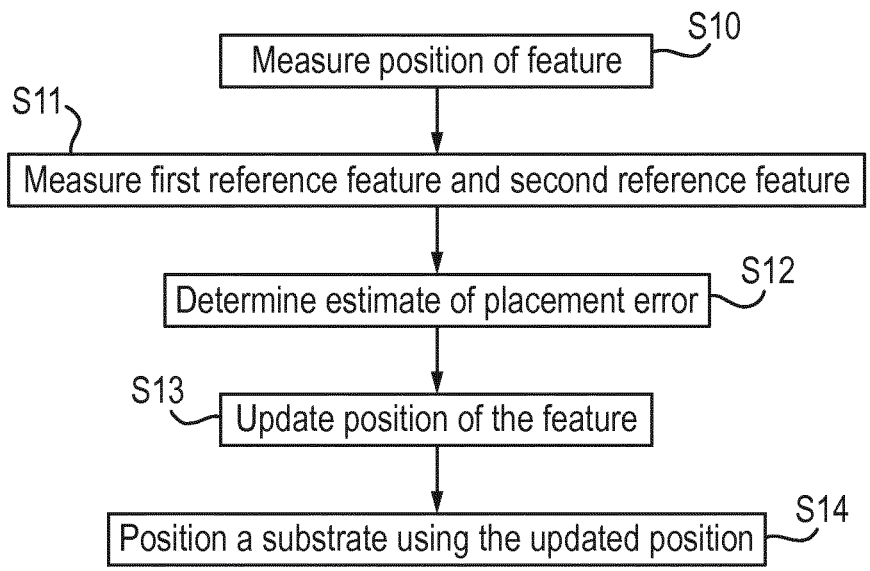
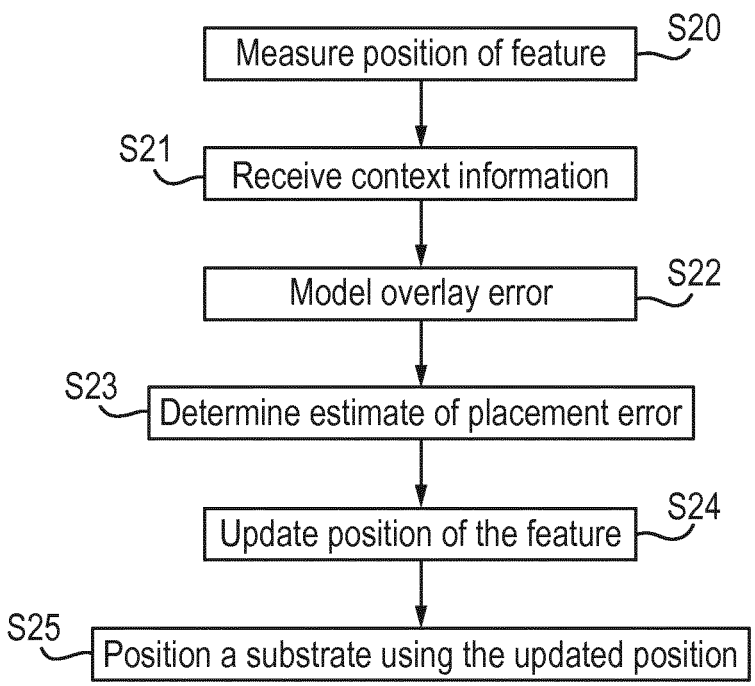

First mark    Second mark

First mark    $s \neq d$    Second mark

First mark    Second mark

METHOD OF DETERMINING A POSITION OF A FEATURE

CROSS-REFERENCE TO RELATED APPLICATIONS

This application is the U.S. national phase entry of PCT patent application no. PCT/EP2017/080190, which was filed on Nov. 23, 2017, which claims the benefit of priority of European patent application no. 16206732.6, which was filed on Dec. 23, 2016 and which is incorporated herein in its entirety by reference.

BACKGROUND

Field of the Invention

The present invention relates to a method, system and program for determining a position of a feature referenced to a substrate and methods, system and programs for controlling positioning of a substrate.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. These target portions are commonly referred to as "fields".

In lithographic processes, it is desirable to frequently measure the structures created forming a circuit pattern, e.g., for process control and verification. Various tools for making such measurements are known, including scanning electron microscopes, which are often used to measure critical dimension (CD), and specialized tools to measure overlay, which is the accuracy of alignment of two layers in an at least partially patterned substrate.

Various techniques can be used to measure performance of the lithographic process. This in turn allows sophisticated process corrections to be included in the control of the operations performed by the lithographic apparatus. For example, a feedback system as described below is generally known for making corrections to the positioning of the substrates in the system by measuring the positioning error between two different layers of the substrate. The positioning error between the two different layers of the substrate is called the overlay error.

Before exposure of a substrate, the substrate is aligned. The goal of the alignment is to determine, for each substrate, the field centres and local distortions, to limit overlay error between layers of the substrate. This is accomplished by measuring alignment marks that are printed on at least one layer of the substrate. The difference between the expected and measured location of the alignment marks is used as the input for the alignment model. The alignment model (which may be based on a linear or higher order alignment) gives an output comprising parameters used for optimizing the position of the substrate during subsequent exposure of the substrate.

To further control the errors in positioning, a feedback system is used often called an automated process control (APC) system. The APC system measures the overlay error for a number of substrates and determines corrections required to reduce the overlay error. These corrections are then used as input for future exposures. The APC system typically includes high-order corrections per exposure. The APC system is intended to correct slowly changing overlay errors as overlay error measurement is done only on a per lot basis. The APC system is intended to correct for varying effects from layer to layer and from lot to lot.

These corrections typically correct for deformation of the substrate due to, for example, process variations, clamping variations and/or temperature variations. These effects can vary significantly per substrate and the process of using the lot based APC control for the overlay error still results in undesirable errors in the positioning of the substrate.

Furthermore, variations can be introduced due to temperature changes in a projection system of lithographic apparatus. The temperature changes can affect the illumination conditions which affects different marks in different ways. Although the APC control attempts to account for these variations, there are still undesirable errors due to temperature changes across the projection system.

SUMMARY OF THE INVENTION

The present invention has the aim of improving determining the position of a feature referenced to a substrate and improving controlling positioning of a substrate.

According to an aspect of the invention, there is provided a method for determining a position of a feature referenced to a substrate, the method comprises: obtaining a measured position of the feature, wherein the feature is configured to enable positioning of the substrate; receiving an intended placement of the feature; determining an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and determining an updated position for the feature using the estimate of the placement error and the measured position of the feature.

According to another aspect of the invention, there is provided a system comprising a processor configured to determine a position of a feature referenced to a substrate, the processor configured to: measure a position of the feature, wherein the feature is configured to enable positioning of the substrate; receive an intended placement of the feature; determine an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and determine an updated position for the feature using the estimate of the placement error and the measured position of the feature.

According to another aspect of the invention, there is provided a program for controlling determining a position of a feature referenced to a substrate, the program comprises instructions for carrying out the steps of: measuring a position of the feature, wherein the feature is configured to enable positioning of the substrate; receiving an intended placement of the feature; determining an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and determining an updated position for the feature using the estimate of the placement error and the measured position of the feature.

According to another aspect of the invention, there is provided a method for controlling positioning of a substrate, comprising: providing a substrate with a first mark and a second mark on one layer of the substrate, wherein the first mark is different from the second mark; determining a relative shift of the first mark with respect to the second mark; and controlling positioning of the one layer of the substrate, a further layer of the substrate or a layer of a further substrate based on the determined relative shift.

According to another aspect of the invention, there is provided a method for controlling positioning of a substrate, comprising: providing a substrate with a first mark on a first layer and a second mark on a second layer of the substrate, the second mark comprising at least one first portion and at least one second portion; determining the position of the first mark; determining a relative shift of the at least one first portion with respect to the at least one second portion; and controlling positioning of the first layer or a further layer of the substrate or any layer on a further substrate based on the determined position and the determined relative shift. According to another aspect of the invention, there is provided a system comprising a processor configured to control positioning of a substrate, the processor being configured to: determine a relative shift of a first mark with respect to a second mark, wherein the first mark and the second mark are on one layer of a substrate, wherein the first mark is different from the second mark; and control positioning of a further layer of the substrate or a layer of a further substrate using the determined relative shift.

According to another aspect of the invention, there is provided a program for controlling positioning of a substrate, the program comprising instructions for carrying out the steps of: determining a relative shift of a first mark with respect to a second mark, wherein the first mark and the second mark are on one layer of a substrate, wherein the first mark is different from the second mark; and controlling positioning of a further layer of the substrate or a layer of a further substrate using the determined relative shift.

According to another aspect of the invention, there is provided a system comprising a processor configured to control positioning of a substrate, the processor being configured to: provide a substrate with a first mark on a first layer and a second mark on a second layer of the substrate, the second mark comprising at least one first portion and at least one second portion; determine the position of the first mark; determine a relative shift of the at least one first portion with respect to the at least one second portion; and use the determined position and the determined relative shift to control positioning of the first layer or a further layer of the substrate or any layer on a further substrate.

According to another aspect of the invention, there is provided a program for controlling positioning of a substrate, the program comprising instructions for carrying out the steps of: providing a substrate with a first mark on a first layer and a second mark on a second layer of the substrate, the second mark comprising at least one first portion and at least one second portion; determining the position of the first mark; determining a relative shift of the at least one first portion with respect to the at least one second portion; and using the determined position and the determined relative shift to control positioning of the first layer or a further layer of the substrate or any layer on a further substrate.

BRIEF DESCRIPTION OF THE DRAWINGS

Embodiments of the invention will now be described, by way of example only, with reference to the accompanying schematic drawings in which:

FIG. 2 is a flowchart of a method of determining and using an updated position of a feature of a substrate;

FIG. 3 is a flowchart of a method of determining and using an updated position of a feature of a substrate;

DETAILED DESCRIPTION OF EXEMPLARY EMBODIMENTS

Before describing embodiments of the invention in detail, it is instructive to present an example environment in which embodiments of the present invention may be implemented. The invention can be applied, for example, in controlling a process step in a lithographic manufacturing process. The invention can be applied for example to control a lithographic apparatus, when applying patterns at locations across one or more substrates. A lithographic process for the manufacture of semiconductor devices will be described to provide an exemplary context in which the method can be used. The principles of the present disclosure can be applied in other processes without limitation.

Figure 1:
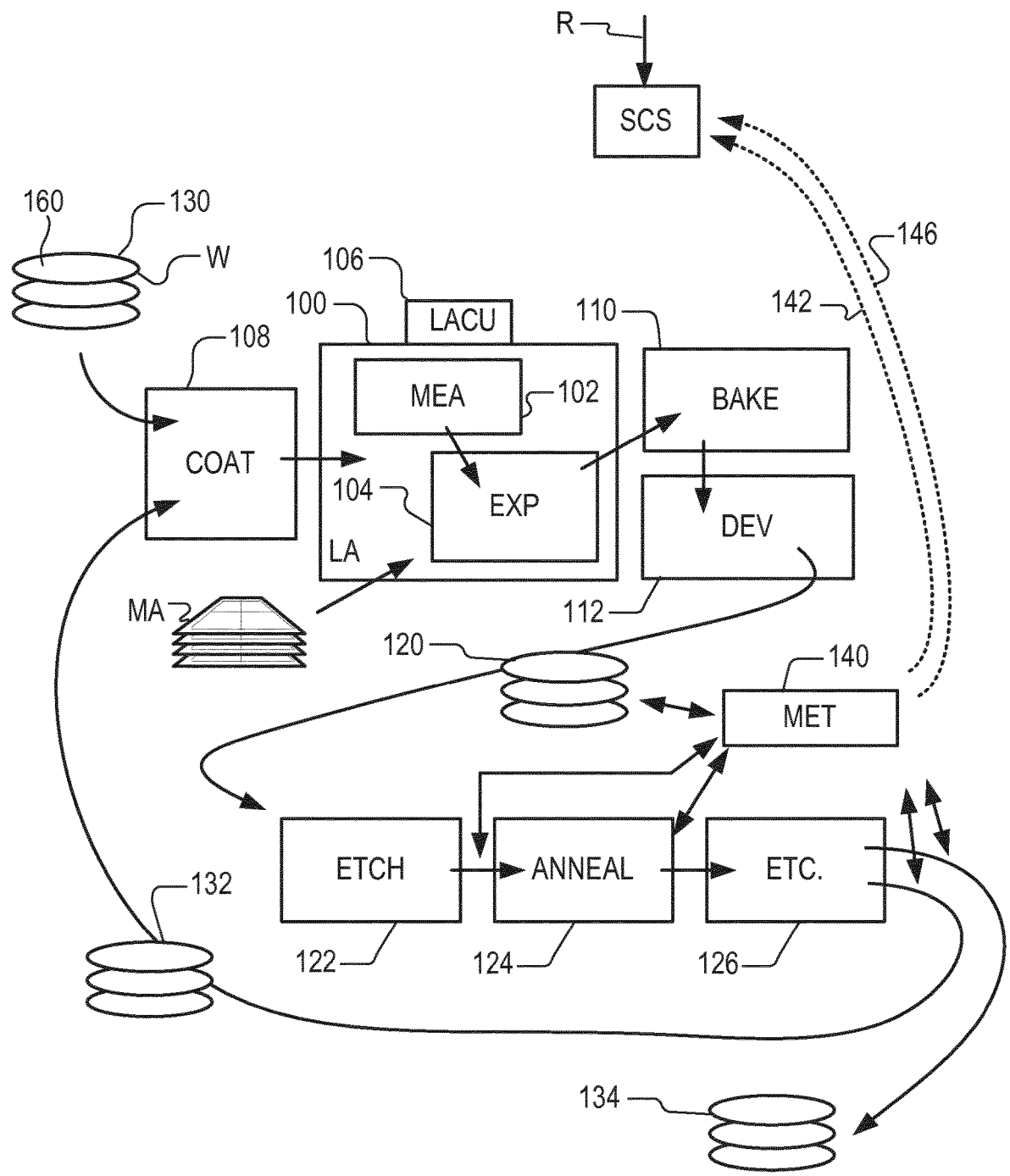
FIG. 1 depicts a lithographic apparatus together with other apparatuses forming a production facility for semiconductor devices, as an example of a system in which an embodiment of the invention may be used.

FIG. 1 shows a lithographic apparatus LA at 100 as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 100 for short), a measurement station MEA is shown at 102 and an exposure station EXP is shown at 104. A control unit LACU is shown at 106. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material on a substrate.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, and/or for other factors such as the use of an immersion liquid or the use of a vacuum. In general the projection system is referred to as the "lens" throughout this document, and these terms are interchangeable. The patterning device MA may be a mask or reticle, which imparts a pattern to a radiation beam transmitted or reflected by the patterning device MA. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU controls all the movements and measurements of various actuators and sensors, causing the apparatus to receive substrates W and reticles MA and to implement the patterning operations. Control unit LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the lithographic apparatus LA.

Before the pattern is applied to a substrate at the exposure station EXP, the substrate is processed at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the alignment marks may deviate from the ideal grid. Consequently, in addition to measuring position and orientation of the substrate, the alignment sensor in practice must measure in detail the positions of many marks across the substrate area, if the apparatus is to print product features at the correct locations with very high accuracy.

The lithographic apparatus LA may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor is not capable of measuring the position of the substrate table while it is at the measurement station as well as at the exposure station, a second position sensor may be provided to enable the positions of the substrate table to be tracked at both stations. Alternatively, the measurement station and exposure station can be combined. For example, it is known to have a single substrate table, to which a measurement stage is temporarily coupled during the pre-exposure measuring phase. The present disclosure is not limited to either type of system.

Within the production facility, apparatus 100 forms part of a "litho cell" or "litho cluster" that contains also a coating apparatus 108 for applying photosensitive resist and other coatings to substrates W for patterning by the apparatus 100. At an output side of apparatus 100, a baking apparatus 110 and developing apparatus 112 are provided for developing the exposed pattern into a physical resist pattern. Between all of these apparatuses, substrate handling systems take care of supporting the substrates and transferring them from one piece of apparatus to the next. These apparatuses, which are often collectively referred to as the "track", are under the control of a track control unit which is itself controlled by a supervisory control system SCS, which also controls the lithographic apparatus via lithographic apparatus control unit LACU. Thus, the different apparatuses can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 120 are transferred to other processing apparatuses such as are illustrated at 122, 124, 126. A wide range of processing steps are implemented by various apparatuses in a typical manufacturing facility. For the sake of example, apparatus 122 in this embodiment is an etching station, and apparatus 124 performs a post-etch annealing step. Further physical and/or chemical processing steps are applied in further apparatuses, 126, etc. Numerous types of operation can be required to make a real device, such as deposition of material, modification of surface material characteristics (oxidation, doping, ion implantation etc.), chemical-mechanical polishing (CMP), and so forth. The apparatus 126 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 130 arriving at the litho cluster may be newly prepared substrates, or they may be substrates that have been processed previously in this cluster or in another apparatus entirely. Similarly, depending on the required processing, substrates 132 on leaving apparatus 126 may be returned for a subsequent patterning operation in the same litho cluster, they may be destined for patterning operations in a different cluster, or the substrate 134 may be finished products to be sent for dicing and packaging.

Each layer of the product structure requires a different set of process steps, and the apparatuses 126 used at each layer may be completely different in type. Further, even where the processing steps to be applied by the apparatus 126 are nominally the same, in a large facility, there may be several supposedly identical machines working in parallel to perform the step 126 on different substrates. Small differences in set-up or faults between these machines can mean that they influence different substrates in different ways. Even steps that are relatively common to each layer, such as etching (apparatus 122) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell is located also includes metrology system MET which receives some or all of the substrates W that have been processed in the litho cell. Metrology results are provided directly or indirectly to the supervisory control system (SCS) 138. If errors are detected, adjustments may be made to exposures of subsequent substrates, especially if the metrology can be done soon and fast enough that other substrates of the same lot are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 140 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 120 prior to etching in the apparatus 122. Using metrology apparatus 140, it may be determined, for example, that important performance parameters such as overlay or critical dimension (CD) do not meet specified accuracy requirements in the developed resist. Prior to the etching step, the opportunity exists to strip the developed resist and reprocess the substrates 120 through the litho cluster. As is also well known, the metrology results 142 from the metrology apparatus 140 can be used to maintain accurate performance of the patterning operations in the litho cluster, by supervisory control system SCS and/or control unit LACU 106 making small adjustments over time, thereby minimizing the risk of products being made out-of-specification, and requiring re-work. Of course, metrology apparatus 140 and/or other metrology apparatuses (not shown) can be applied to measure properties of the processed substrates 132, 134, and incoming substrates 130.

In the example of a lithographic manufacturing process, the substrates are semiconductor wafers or other substrates to which patterns are to be applied in a patterning step, and structures formed by physical and chemical process steps.

In a first embodiment, at least one feature 160 may be provided on a surface of a substrate 120, 132, 132, 134 to enable positioning of the substrate. The feature 160 may be a specific feature intended for alignment, or any other feature which may be measured to allow the substrate to be aligned, e.g. before exposure. The positioning of the substrate may be carried out using the feature 160. The positioning includes moving the substrate in a variety of ways, including moving the substrate large distances, and/or making very small adjustments to the position of the substrate. A feature 160 is shown on substrate 130 of FIG. 1 but may equally be found on the other substrates depicted in FIG. 1. The feature 160 may be used to align a layer of a substrate to a previous layer (or layers) of the substrate which have already been exposed. The feature 160 is shown as a single feature on the surface of the substrate, but it will be understood that the feature 160 may be part of a grid pattern and/or there may be multiple features 160 on any single substrate layer. The location of the feature 160 is measured to ensure that the substrate is positioned in the correct location when exposure of the substrate 130 is carried out. As already described, any errors in the positioning of the substrate 130 may lead to overlay errors potentially causing yield loss of the lithographic process. As described above, known methods for reducing overlay errors are known and systems such as metrology system 140 and supervisory control system SCS may already be in place to minimize overlay error.

Although the feature 160 is placed on the substrate as accurately as possible, during exposure of the feature 160 there will normally be an error in the placement of the feature 160. This can be referred to as the placement error. The placement error is the difference between an intended placement of the feature 160 and an actual placement of the feature 160. This means that the feature 160 is not printed exactly at the desired location. Thus, when using the feature 160 to position a substrate 130 and aligning a subsequent layer of the substrate (or a layer of a further substrate), the layer will not be at the exact position where it is expected. Thus, any resulting position corrections based on the alignment measurements will contain the placement error.

The placement error may be determined in different ways. For example, lens (i.e. projection system) and/or patterning device MA distortions can cause an overlay error having a certain fingerprint across a field (intrafield fingerprint). An overlay fingerprint is the overlay error across the fields of the substrate. The overlay fingerprint may vary across the fields and/or substrates because it depends on the state of the substrate 130, projection system and/or patterning device MA which will typically change during exposure of substrates 130. The overlay fingerprint may change during exposure due to the (non-uniform) temperature increases of the substrate 130, patterning device MA and/or the projection system. These distortions within the field are typically high-order, meaning that the centre of the field is not necessarily displaced, but the shape of the field may be distorted. Depending on where the intended placement of the feature 160 is on the substrate 130, this will mean there is a placement error which varies per lot of substrates, per substrate, per layer and even per field of the substrate.

An error in the placement of a feature used to align layers of a substrate can lead to overlay error. An error in the placement means that there is a difference between the intended location of the features used to position the layers, and the actual location of the features used to position the layers. The error in the placement of these features can lead to each of the layers being positioned in slightly incorrect location for exposure, thus leading to overlay error. The automated process control (APC) system will try to account for this error as it will control part of the static and drifting part of the overlay error. However, the APC system may not be able to control overlay error variations between substrates. When overlay is critical between two layers of a substrate, and those layers align to alignment markers in different layers, or use different alignment models, this can result in increased overlay variation, i.e. overlay errors. This will reduce the yield of substrates produced by the lithographic apparatus 100. The effect of the placement error could possibly cancel out without affecting overlay if the layers are aligned to alignment markers in the same layers, using the same alignment model and settings of the system measuring the position of the alignment markers (e.g. wavelength of radiation used to measure and the order wherein the markers are measured). However, this is not always possible or desirable and imposes unrealistic physical constraints. The method described in the embodiments has fewer constraints and thus increase design freedom.

A variation in intrafield distortions and/or translation and/or rotations of the field during placement of the feature 160 results in variation during exposure of layers of the substrate which are aligned to that feature 160. When the position of the feature 160 is measured, the displacement of the feature may be interpreted as an overlay error and thus, the field centres will be erroneously "corrected" based on a translation error. Thus the placement error may cause an incorrect "correction" which affects alignment of the substrate which contributes to overlay error. Presently known systems do not adequately account for the placement error.

In an embodiment, a method is provided for determining a position of a feature reference to a substrate. The method comprises measuring a position of the feature, wherein the feature is configured to enable positioning of the substrate. The method further comprises receiving an intended placement of the feature and determining an estimate of a placement error. The placement error is the difference between the intended placement of the feature and an actual placement of the feature. The placement error can be determined based on knowledge of a relative position of the first reference feature reference to a first layer with respect to a second reference feature reference to a second layer, wherein the first layer and the second layer are on a substrate. The method further comprises determining an updated position for the feature using the estimate of the placement error and the measured position of the feature. The feature 160 being referenced to a substrate 130 may mean that the feature is on a substrate 130, e.g. located on a layer of a substrate 130. The first reference feature and the second reference feature being referenced to a first layer and second layer respectively may mean that the first reference feature is on the first layer and the second reference feature is on the second layer.

By using both the measured position of the feature and determining an estimate of the placement error, a more accurate position of the feature (i.e. the updated position) can be determined. As described, despite the above described known systems for correcting and reducing positioning errors, there is a further problem that errors can be introduced when the feature is formed on the substrate. Using the method described above allows the system to account for the error in forming the feature on the substrate (placement error) which is later used to position the substrate. This is particularly beneficial as it can be used as part of a feedforward and/or feedback system to more accurately position further layers of the substrate and/or further substrates respectively. The updated position may be used for controlling a position of a substrate. This may be particularly useful for example for a step of patterning the substrate. For example, this could be used in a manufacturing process, such as a lithographic manufacturing process, of the type described in relation to FIG. 1.

The method allows for the error in placing the feature 160 on the substrate 130 to be accounted for. The feature may be provided on a layer of any of the substrate 120, 130, 132, 134 shown in FIG. 1. The method allows the error to be determined as part of a feedback loop or feedforward loop for positioning the layer of the substrate 130 comprising the feature 160, and/or further layers of the same substrate 130 and/or a layer of a further substrate 130. The feedback loop may use the updated position for determining an updated position for further substrates. The feedforward loop may use the updated position for exposing further layers on the same substrate, i.e. the substrate comprising the first reference feature and second reference feature. Thus, the updated position may be used as part of a feedback and/or feedforward loop. The method is beneficial even for a single layer of the substrate 130 comprising the feature 160 because the substrate 130 is more accurately positioned for exposing the layer comprising the feature 160. For each feature 160, there might be a corresponding correction for the placement error of the feature 160.

The updated position can be used as an input for the alignment model described above. In other words, when the position of a feature 160 is measured, the updated position can be used as the input for the alignment model rather than the measured position of the feature 160. In this way, the placement error is accounted for. Using the updated position means that the placement error does not impact the alignment modelling and alignment corrections during exposure of the layer of the substrate 130 and also during exposure of further layers of the substrate 130 and/or further substrate(s). Thus, the method may be a feedforward method which uses the updated position for determining placement of further layers and/or substrates.

The method is useful for determining the updated position of the feature which can be used in various ways is herein described. Most simply, the updated position of the feature 160 may be used to position a substrate 130 on the basis of the updated position of the feature 160. The substrate 130 may be a substrate 130 comprising the first layer and the second layer. The feature 160 may be positioned on the first layer or the second layer. Thus, the substrate 130 comprising the feature 160 on the first layer or the second layer, for example, may be positioned to align the first layer or the second layer of the substrate 130 respectively as desired. The method may further comprise exposing the first layer of the substrate 130 to conditioned radiation. This means that the first layer can be more accurately positioned to take into account the placement error of the feature 160 used to align the substrate 130.

Alternatively, the feature 160 may be located on another layer of the substrate 130 comprising the first layer and/or the second layer, i.e. the feature 160 may be on the same substrate 130 as the first reference feature and the second reference feature but on a different layer. Thus, the method may be used to position a further layer on the same substrate based on the placement error calculated for a feature 160 on a previous layer. Alternatively, the feature 160 may be on a layer of a different substrate i.e. the feature 160 may be on a further substrate for which no measurement of the first and second reference feature is performed. Thus, the method may be used to position a further substrate based on the placement error calculated on a previous substrate. In other words, the position of the feature may be measured on a substrate different from the substrate associated with the determined estimate of the placement error. Thus, the error estimated for one substrate can be used to update a position of a feature 160 on another substrate.

The feature 160 may be on the first or the second layer of the further substrate. Thus, the feature 160 may be placed on an equivalent layer to the first layer or the second layer, but on a different substrate. For example, the first layer may in fact be a fourth layer to be exposed on the substrate and thus, the first reference feature may be placed on the fourth layer of a substrate and the feature may be placed on the fourth layer of another substrate. Alternatively, this may apply to the second layer rather than the first layer. It will be understood that the example of the fourth layer could be replaced with any layer, including the first, second, third and so on.

The estimate of the placement error may be applied to selected features on selected layers and/or substrates. Thus, it is possible to preselect the features to which the placement error is applied. E.g. the updated position and/or estimate of the placement error could be applied during exposure of all layers of all substrates in one lot, or even several lots.

As described above, the method for determining the updated position of the feature 160 may be particularly useful because it can be used in a feedforward or feedback system to determine positioning of further layers and/or further substrates. This means that the placement error for one feature 160 (or for several features on one layer of a substrate 130) may be used to more accurately position further layers on the substrate and/or substrates. This is beneficial because it is not necessary to determine the placement error for each layer or even for each substrate. Furthermore, once the placement error has been determined, this can be used for further alignments even after the layer comprising the feature 160 has been exposed. Advantageously, this means that measurements to determine the placement error may not be required on further layers and/or substrates. Reducing the number of measurements reduces the time taken to produce semiconductor devices (i.e. fully processed substrates) which is preferable. In general, the placement error might be used for determining the placement error of further features, even if further measurements or models are used, and can still be beneficial in reducing the number of measurements and/or amount of modelling required to determine further placement errors/updated positions.

The estimate of the placement error may be determined in various different ways. As already described, the estimate is based on a knowledge of a relative position of a first reference feature referenced to a first layer on a substrate with respect to a second reference feature referenced to a second layer of the substrate. In other words, the placement error is calculated using a feature from two different layers of a substrate. As indicated above, the first layer and the second layer may be different from the layer on which the feature 160 is located. The first layer is a different layer than the second layer such that the overlay can be determined between the first layer and the second layer. The first layer and the second layer may be adjacent to each other, or may have one or more layers between them.

The first reference feature, the second reference feature and/or the feature 160 may be a grating. The features may otherwise be referred to as marks. The first reference feature and the second reference feature may be the same type of feature as each other. The first reference feature and the second reference feature may not be of the same type as the feature 160 for which the placement error is estimated. For example, the first reference feature and the second reference feature may not be used, or capable of being used, to align the substrate 130. The first reference feature and/or the second reference feature may be a feature used to measure overlay, e.g. the first reference feature and the second feature may be gratings, optionally, overlay marks or optionally product features usable to determine an overlay error. The first reference feature and/or second reference feature may be overlay marks configured to provide overlay feedback to the APC system. Additionally or alternatively, the feature 160 may be a grating, e.g. an alignment mark.

The method may comprise measuring the first reference feature and the second reference feature to determine an overlay error between the first layer and the second layer. Thus, the method may comprise directly measuring the first reference feature and the second reference feature to determine the placement error. The first reference feature and the second reference feature may be used to determine the overlay error between the first layer and the second layer. Thus, the overlay error may effectively be measured at the location of the first reference feature and the second reference feature. This could be done for example by the APC system described above. For example, results 146 relating to the measurements of the first reference feature and the second reference feature may be sent from the metrology apparatus 140 to the APC system. The method may use the measured overlay error to determine the estimate of the placement error. For example, the estimate of the placement error may be the same as the measured overlay error i.e. the estimate of the position error and the overlay error may be one-to-one. Alternatively, the estimate of the placement error may be a function of the measured overlay error, or may comprise the measured overlay error. Processing steps may be required to determine the placement error based on the overlay error. The overlay error may not be equal to the placement error, for example, due to different sensitivities of the feature 160 and the reference feature regarding variations in process conditions and projection system aberrations.

An exemplary implementation of a method in accordance with an embodiment is depicted in FIG. 2. In S10 the position of the feature 160 is measured. This step could be carried out before, after or at the same time as step S11. In S11, the first reference feature and the second reference feature are measured as described above. The measured first reference feature and second reference feature may be used to determine the estimate of the placement error in S12. In S13, the measured position of the feature from S10 and the estimate of the placement error from S12 may be used to calculate an updated position of the feature. As previously described, the feature may be on one of the first layer or the second layer, the feature may be on another layer of the substrate comprising the first layer and the second layer (i.e. a further layer of the same substrate), or the feature may be on a layer of a substrate not comprising the first layer and the second layer (i.e. a layer of a further substrate). Thus, the updated position of the feature 160 can be used to position any of the layers comprising the feature 160 in S14.

Alternatively, the method may further comprise modelling an overlay error between the first layer and the second layer and determining the first and second feature using the modelled overlay error. The method may comprise using an overlay model to determine the overlay error across at least a part of the substrate 130. The modelled overlay error across the substrate 130 may be used to extract the modelled position of the first feature and the second feature. The overlay error may be modelled in various different ways. For example, the method may comprise receiving context information and/or lithographic apparatus information, and using the context information and/or lithographic apparatus information to model the overlay error. The context information and/or lithographic apparatus information relates to measured and/or modelled deformation of at least one of the substrate, a mask and/or the projection system. The context information and/or lithographic apparatus information may include results 146 of measurements from the metrology system 140, and/or from the lithographic apparatus LA 100. Modelling the overlay error may comprise using a predetermined value. This could be based, for example, on previous overlay data, on average overlay errors for multiple substrates or lots of substrates or average overlay errors between particular layers of substrate.

The method may use the modelled overlay error to determine the estimate of the placement error. Measurements may be taken from convenient measurement location(s) on the substrate 120. Modelling the overlay to determine the position of the first reference feature and the second feature has the further advantage that the location of the first reference feature and the second reference feature are not limited to being near the feature 160 and the first reference feature and second reference feature may be located elsewhere away from the feature 160. The method may use the modelled overlay error to determine the estimate of the placement error. For example, the estimate of the placement error may be the same as the modelled overlay error, i.e. the estimate of the position error and the overlay error may be one-to-one. Alternatively, the estimate of placement error may be a function of the modelled overlay error, or may comprise the modelled overlay error. Processing steps may be required to determine the placement error based on the overlay error.

An exemplary implementation of a method in accordance with an embodiment is depicted in FIG. 3. In S20 the position of the feature 160 is measured. This step could be carried out before, after or at the same time as either of the steps in S21 or S22. In S21, context information and/or lithographic apparatus information may be received as described above and this may be used to determine an overlay error in S22. Determining the overlay error may comprise calculating a model of the overlay error between a first layer and a second layer to calculate a modelled position of a first reference feature and a position of a second reference feature. The estimate of the placement error can then be determined based on the modelled positions of the first reference feature and the second reference feature in S23. In S24, the measured position of the feature from S20 and the estimate of the placement error from S23 can be used to calculate an updated position of the feature. As previously described, the feature 160 may be on one of the first layer or the second layer, the feature 160 may be on another layer of the substrate comprising the first layer and the second layer (i.e. a further layer of the same substrate), or the feature 160 may be on a layer of a substrate not comprising the first layer and the second layer (i.e. a layer of a further substrate). Thus, the updated position of the feature 160 can be used to position any of the layers comprising the feature in S25. It is noted that certain steps of FIG. 3, e.g. S20, S24, S25 may be carried out in the same way as the corresponding steps of FIG. 2, e.g. S10, S13 and S14 respectively.

In further detail, for each exposed lot, only a few substrates may be selected and measured on the metrology apparatus 140 to determine the error of overlay-targets on the substrate. The overlay-targets may be marks or features which are similar to the first reference feature and the second reference feature. These measurements can be input to the APC system to determine feedback overlay corrections for future exposures. Since only a few overlay-targets may be measured per lot, e.g. a few hundred, an extrapolation and/or interpolation can be used to estimate the overlay fingerprint for each field for each substrate as an input for the APC system. The extrapolation and/or interpolation from a few hundred points per substrate can be done by fitting a mathematical model over measured points. The resulting overlay fingerprint can be used to determine a modelled first reference feature position and a modelled second reference feature position for determining the feature 160.

The overlay fingerprint may be a product of the existing APC systems. The estimate of the placement error for each feature 160 can be estimated as a function of the local overlay error: $f_1$ (OverlayFingerprint(x,y)). This may provide a unique estimate of the placement error for each unique overlay fingerprint. There may be a unique overlay fingerprint per substrate table (for example, because the APC system has a particular correction loop for a particular substrate table), per lot, or per substrate depending on the overlay control method which is used to determine the overlay fingerprint. As described, the simplest function would be a multiplication by 1, where the estimate of the placement error is estimated to be the same as the overlay error. More accurate estimations of $f_1$ can be determined by correlating overlay errors with placement errors in either experiments or simulations. The overlay fingerprint can optionally be refined by using context information and/or lithographic apparatus information, e.g. the results from $f_1$ (OverlayFingerprint(x,y)) can be refined using context information and/or information from the lithographic apparatus LA of 100 $f_2$ (Context information and/or lithographic apparatus information) The refinement can, for example, result in placement error corrections per substrate where overlay fingerprint information is only available per substrate table and/or lot. Refinement can also result in a more accurate estimate of the placement error per feature 160.

To reduce the amount of measurements needed, typically the overlay corrections can be averaged per lot or substrate table instead of per substrate. Heating of the patterning device MA and/or a projection system are known to increase errors. As described, these errors can result in a placement error when forming a feature 160. Overlay measurements can be carried out on one or more substrates per lot, e.g. 4 substrates per lot. To refine the results, a function $f_2$ (Context information and/or lithographic apparatus information) can be used to extrapolate the overlay fingerprint to determine what the fingerprint is expected to be for other layers or substrates not measured. A part of this calculation can use context information and/or lithographic apparatus information referred to above, including parameters related to patterning device MA and/or projection system heating. This enables determination of a unique estimate of the placement error for each feature per substrate while only 4 substrates were measured.

Alternatively, corrections can be determined per substrate, as herein described. The correlation between the placement error and the overlay fingerprint may depend on the parameters included in the context information and/or lithographic apparatus information. The context information and/or lithographic apparatus information may include, but is not limited to, substrate table and/or projection system dynamics, and heating effects of the patterning device MA and/or the projection system and/or a substrate. The context information and/or lithographic apparatus information can be measured (i.e. logged) or can be modelled. For example only, the feature 160 is likely to have a different design to the first reference feature and to the second reference feature. This means that the light used to image the feature may take a different path through the projection system than the light used to image the first reference feature and the second reference feature. Therefore, a projection system aberration may have a different effect on the feature 160 and the first and second reference features. The different effects can both be measured or simulated (i.e. modelled) for several aberrations and designs. During exposure the projection system aberrations may be measured and this information can be combined with the measured/modelled context information and/or lithographic apparatus information to refine the estimate of the placement error per feature 160.

The temperature of the projection system may change whilst multiple substrates are exposed within a lot, i.e. in a batch. More specifically, the projection system temperature generally increases within a lot from the first substrate to the last substrate. In spite of arrangements to maintain a constant projection system temperature, a small temperature change may occur (e.g. depending on the illumination conditions) which is nevertheless significant for forming patterns with very small features. For example, it is know that relatively intense illumination can have significant heating effects especially when there are extreme dipole illumination settings which may induce projection system heating. The heating of the projection lens may lead to introduction of lens aberrations, typically referred to as Zernike aberrations which are associated with characteristic imaging effects. For example a Zernike Z7 aberration is referred to as coma and typically associated with imaging shift effects; e.g. features are printed at a location which is shifted with respect to a desired (nominal) location.

When structures, such as overlay marks, alignment marks, and/or product features have high sensitivities to Zernike aberrations, the structures will be printed on the substrate with an unintended shift. As the temperature of the projection system changes, the unintended shift will change, e.g. drift, throughout the lot. The shift can be very dynamic and may depend on many parameters, which means that it is not possible to apply process corrections (for example, using APC) to the entire lot to sufficiently account for the effects of the shift.

Various correction methods based on prediction of the lens heating evolution may be used to reduce or minimize the effects of temperature changes in the projection system. However, even if these methods are used, errors relating to the temperature change across the projection system (which may be referred to as projection system induced errors) may still remain (for example due to the limited accuracy of such a lens heating prediction method). When the exposed, i.e. printed, structures are sensitive to (at least one) Zernike aberration(s), the projection system induced errors may cause an image shift. Furthermore, different structures at different sizes have different sensitivities. In other words, different structures may respond to the temperature changes in the projection system in different ways, which makes it even harder to compensate for temperature changes. For example, different types of structure, e.g. product features, alignment marks and/or overlay marks, may have different sensitivities. Even different marks of the same type (i.e. which may be used for a similar purpose) for example, two alignment marks, may have different Zernike sensitivity values. In this context, the Zernike sensitivity value is an indication of the sensitivity of the mark to aberration/temperature changes in the projection system.

The projection system induced error, e.g. translation drift, could occur when variation of temperature in the projection system occurs and alignment marks with a high sensitivity to aberrations are used. This issue may be a particular problem when certain types of feature are being exposed, for example, when creating memory (DRAM) because the layers may be exposed using extreme dipole illumination conditions. It is generally desirable to reduce the overall imaging shift error between layers, e.g. the overlay error. Even relatively small potential overlay drift of 1.5 nm for example, due to projection system induced errors are undesirable and in some cases, unacceptable.

In an embodiment, a first mark and a second mark for a single layer mark are designed such that the shifts in the first mark and/or the second mark which occur during the exposure of this single layer mark with the first mark and the second mark due to projection system heating are indicative of the imaging shift associated with the projection system heating. As described below, relative shifts between the first mark and the second mark and/or a portions of either mark may be determined for a layer of a substrate and may be used for controlling positioning of a further layer of the substrate, e.g. the second layer. Thus, the projection system induced errors may be corrected for in further layers/substrates. This will have the benefit of reducing errors in the marks printed on the substrate. For example, this may reduce the error in placement of the alignment mark such that the alignment mark is more accurately placed to the reference structure, like device pattern, which can reduce overlay and improve throughput. The relative shift is the difference between the absolute distance between a first mark and a second mark in one single layer mark and is mostly contributed by the aberration sensitivity difference between the first and second mark.

As already described, it can be beneficial to more accurately position an alignment mark on a layer of a substrate for positioning the substrate. It is known that different structures, for example, an alignment mark and a product feature, may be affected by variations in the projection system in different ways. The present method takes advantage of the difference in the effect on different types of structure. Thus, in a second embodiment a method for controlling positioning of a substrate is provided. The method comprises providing a substrate with a first mark and a second mark on one layer of the substrate. The first mark is different from the second mark. The method further comprises determining a relative shift of the first mark with respect to the second mark. The first mark and the second mark may be on the same layer, and may thus, be collectively referred to as a single layer exposure mark. The method comprises controlling positioning of the one layer of the substrate, a further layer of the substrate or a layer of a further substrate based on the determined relative shift. Optionally, the method further comprises determining a projection system induced error using the determined relative shift [for example often a linear relationship exists between a Zernike aberration and the determined relative shift. Thus, the step of controlling position of a substrate may be carried out using the relative shift and/or the projection system induced error. Knowledge of the relationship allows determination of the projection system induced error (aberration) based on the determined relative shift. For example, in more detail, the relative shift can be determined by lens aberration (Zernikes) and aberration sensitivity. For example, for lithographic effects which are linear with aberration, the sensitivity of nth order Zernike may be:

$$\frac{\text{displacement of } n\text{th order} - \text{the displacement of an ideal lens}}{n\text{th order Zernike}}$$

The first mark may otherwise be referred to as a first pattern or a first mark pattern. The second mark may otherwise be referred to as a second pattern or a second mark pattern.

Figure 4A:
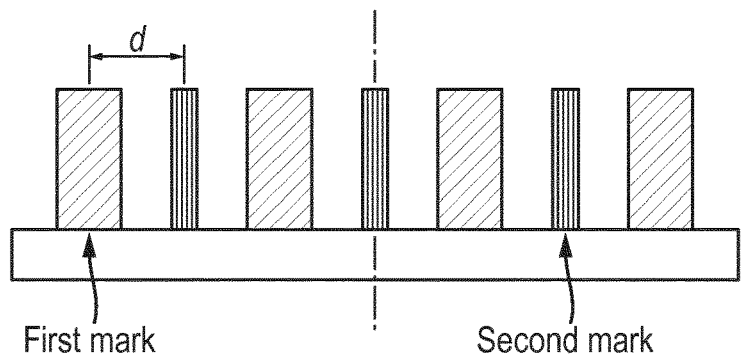
FIG. 4A illustrates the position of a first mark and a second mark when there is no projection system induced error and FIG. 4B illustrates the position of the first mark and the second mark when a projection system induced error has caused a shift of the second mark.
Figure 4B:
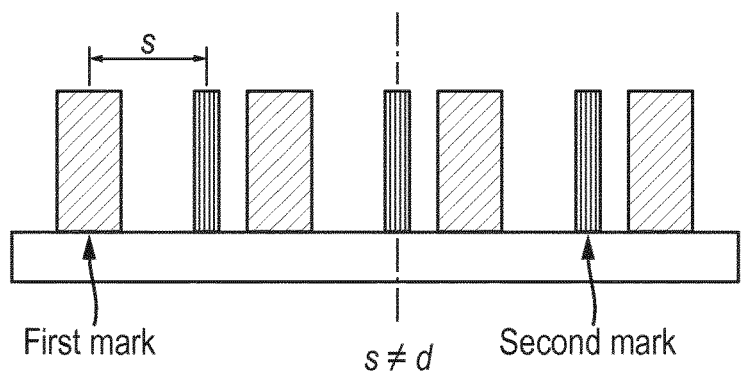

FIGS. 4A and 4B depict an example cross section of the first mark and the second mark on the one layer of the substrate. The depiction in FIGS. 4A and 4B will be described in further detail below, but it is noted that the specific details and relative sizes shown are only exemplary.

The first mark is different from the second mark. This may mean that the first mark and the second mark have different sensitivities to an aberration in the projection system, wherein the projection system is used to expose the first mark and the second mark simultaneously. The first mark and the second mark may differ in various ways to provide the different sensitivities.

In the example shown in FIGS. 4A and 4B, the first mark may have multiple first portions and the second mark may have multiple second portions. In other words, each mark may comprise several portions, i.e. several features. It is not necessary for the first mark and the second mark to each comprise several portions. However, this can be beneficial because it can be easier to detect the shift of the second mark pattern with respect to the first mark. In other words, an average relative shift, which may be based on the relative shift of multiple corresponding portions, may be used to more accurately determine the shift. This is particularly useful for diffraction based measurements described below. The portions which make up each mark may be substantially uniform. Thus, the portions used for the first mark may all be affected by a projection system aberration in the same way, and/or the portions used for the second mark may all be affected by a projection system aberration in the same way. This means that it is simpler to predict how the projection system aberration will affect the first mark and/or the second mark.

In the example shown in FIGS. 4A and 4B, the wider portions are part of the first mark and the narrower portions are part of the second mark. The width of the portions can affect the sensitivity to aberrations in the projection system such that the portions of the first mark have different sensitivity to the portions of the second mark. Additionally or alternatively the sensitivity of the portions may be affected by diffracted pattern difference of exposure (DUV exposure light) and measurement (SMASH WA sensor), due to different patterns (segmentation).

The portions may form a grating. The first mark and the second mark are to be exposed together in the one layer of the substrate. The effect of projection system heating may be present on at least part of the one layer.

Different patterns are indicated in FIGS. 4A and 4B to distinguish between the first mark and the second mark. The patterns shown in these Figures are for distinguishing between the two types of mark only.

Figure 5:
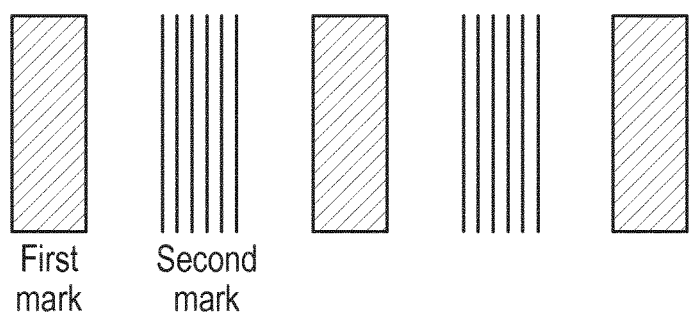
FIG. 5 illustrates an example of the first and second mark.

However, as indicated above, the first mark and the second mark may have different sensitivities and this may be due to a variety of reasons. An example of the different types of portion used for the first mark and the second mark is shown in FIG. 5. As shown, the first mark may comprise multiple first portions and the second mark may have multiple second portions. As shown, at least one of the second portions may comprise a plurality of elements. In other words, the second portion may be segmented into elements. The pitch between the second portions may be larger than the pitch between the plurality of elements. In other words, the distance between each of the second portions may be larger than the distance between elements of the second portions. The pitch between the plurality of elements of the second portion may be approximately the same as the pitch of product features. Thus, the second mark may be a product feature or a feature having a similar response to the projection system induced error as a product feature.

A first portion may comprises fewer elements than a second portion. Furthermore, the first portion may not be segmented at all. Thus, at least one of the first portions may comprise only a single element. This is indicated by the shape of the first portions shown in FIG. 5. Thus the first mark may be an alignment mark or an overlay mark. The pitch between the first portions is much greater than the pitch between individual elements of the second portion.

A single element of a first portion may be larger than a single element of a second portion. This means that for example, when viewed in an X-Y plane, as is shown in FIG. 5, an element of the first portion may have a greater cross sectional area than an element of a second portion. Thus, the different sizes of the elements of the first portion and the second portion may have different sensitivities. A single element of a first portion may correspond in size to the plurality of elements making up a second portion. This means that when viewed in an X-Y plane, a parameter around the element(s) of a first portion may be of substantially similar size to a parameter around the element(s) of a second portion. This is depicted in FIG. 5, because although a plurality of elements may be used to make up portions of the first and/or second mark, each of the portions of the first mark and the second mark have similar lengths and widths overall.

Additionally, the first portions may be substantially consistent in shape and pitch, and the second portions may be substantially consistent in shape and pitch. This means that the first portions are generally the same as each other and have a consistent distance between portions, and the second portions are generally the same as each other and have a consistent distance between portions. The markers may be considered to have a grating like configuration, in other words, the markers may typically have periodic repetition of a portion as depicted in FIGS. 4A, 4B and 5. A periodic aspect of the portions may be useful in particular when using diffractive based measurements on the markers to determine the relative shift between the first marker and the second marker.

Although FIG. 5 depicts that the first mark has multiple first portions and the second mark has multiple second portions, this is for example only. The first mark may have more portions than are shown in FIG. 5, or may have fewer, or even one. The second mark may have more portions than are shown in FIG. 5, or may have fewer, i.e. one.

The first mark and the second mark depicted in FIGS. 4A and 4B are for example only but can be used to illustrate various features relating to the first mark and the second mark. For example, the first mark and the second mark may overlap. This means that when the substrate is viewed perpendicular to the surface of the substrate, the first mark and the second mark appear to be overlapping at least in part. As will be described, this may mean that the first portions and the second portions are interlaced, at least for the overlapping parts of the mark. However, even when overlapping/being interlaced the individual portions of each mark do not overlap. Thus, none of the first portions are in contact with any of the second portions.

It is not necessary that the first mark and the second mark overlap, for example, the first mark and the second mark may be near each other or adjacent to one another, or aligned along one edge. The relative shift between the first mark and the second mark may still be determined without an overlap, but having the marks overlap, i.e. by having the first mark extend across at least part of the second mark, may mean that the shift can be more accurately determined. In general, extension of marker, for example, a grating like marker, enables use of diffraction based metrology, which by definition averages across the whole (at least illuminated) part of the marker. Thus, the overlap may improve accuracy as measurement error may then also be scaled down.

The first mark and the second mark may optimally be at the same level, i.e. exposed at the same time. Ideally, the first mark and the second mark are in the resist (right after exposure) and may be measured in the resist).

As shown in the FIGS. 4A and 4B, the first mark and the second mark may be interlaced, or more specifically, the first portions and the second portions may be interlaced. In other words, the first portions and the second portions may be alternating, as shown in FIGS. 4A and 4B. This may occur due to the overlapping nature of the first mark and the second mark. The first portions and the second portions may be interlaced without having the first portions and the second portions overlap i.e. the first portions do not touch the second portions. In other words, the first mark and the second mark may overlap, but the first portions may not contact or overlap with the second portions. This is preferable because it may not be possible to detect the relative shift of any of the second portions relative to a corresponding first portion if part of the first portion and the second portion are effectively in contact with each other.

The relative shift between the first mark and the second mark is depicted in FIGS. 4A and 4B. FIG. 4A depicts an example of how the first mark and the second mark would be provided if the first mark and the second mark were exposed on the one layer of the substrate when no projection system aberration was present. As shown in FIG. 4A, there is a distance, d, between the centre point of a portion of a first mark and a centre point of a corresponding portion of a second mark. In this example, the corresponding first portion and second portion are adjacent to one another. The distance, d, is the distance between the corresponding portions of the first mark and the second mark when there is no projection system aberration.

When there is a projection system aberration, the first mark and the second mark are affected (i.e. shifted). Because the first mark is different from the second mark, the first mark and the second mark are affected in different ways by the projection system aberration. Thus, the distance between the corresponding portions of the first mark and the second mark is not the same as in FIG. 4A. As shown in FIG. 4B, the distance between the corresponding portions of the first mark and the second mark when there was a projection system aberration during exposure is s. As is clear from FIGS. 4A and 4B, distance s is not the same as distance d. In this example, the distance between the first portion and the corresponding second portion, s, is greater due to the projection system aberration than the distance between the first portion and the second portion, d, when there is no projection system aberration. It is noted that for other combinations of different marks, the distance s may be smaller than the distanced. Thus, there is a relative shift between the first mark and the second mark due to a projection system aberration.

The relative shift depends on the state of the projection system, so that in a case of projection system heating, drift will occur throughout the lot of substrates (i.e. intralot drift). Also the starting state of the projection system will be dependent on the usage of the projection system prior to the lot. Therefore, the actual shift may vary dynamically from one lot to another, or from one substrate to another. As will be described below, using the first mark and the second mark of the present invention, the relative shift can be determined for each lot and each substrate in the lot. The determined relative shift can be fed forward to the next layer(s) for a substrate specific correction.

The relative shift between the first mark and the second mark can be determined in a variety of different ways. For example, the method may determine the relative shift by measuring a position of the first mark and a position of the second mark after they have been exposed and comparing the measured positions to an expected distance between the first mark and the second mark. Thus, the method may comprise measuring the position of the first mark and the second mark and calculating the distance between the first mark and the second mark. The relative shift may then be determined using the calculated distance between the first mark and the second mark and an expected distance between the first mark and the second mark. It is noted that the distance between the first mark and the second mark may be the distance between a first portion and a corresponding second portion, or may be the average (e.g. mean) distance between first portions and corresponding second portions.

The first mark and the second mark may be designed in a way that allows the projection system heating related relative image shift between the first mark and the second mark to be measured using known measurement systems after the marks are exposed. For example, the measurements may be done using Integrated Metrology (IM) or Stand Alone Metrology (SA), typically based on diffractive measurements. Advantageously, the measurements can be carried out on the first mark and the second mark in resist (i.e. before the substrate is processed further, e.g. subjected to etching and/or deposition processes) which means that little or no significant mark degradation is to be expected. This means that the accuracy and precision may be much higher than when measurement of an etched mark is used.

Other methods for determining the relative shift may be used. In another example, the relative shift is determined using diffraction based measurement. A marker comprising portions (which may form a grating), which allows the use of diffraction based measurements which are common in the lithographic industry. A diffraction based measurement method and system is known and herein incorporated by reference in its entirety from U.S. Pat. No. 9,134,256B2. A diffraction based measurement may integrate the shift error across all portions (e.g. an entire grating) and hence use determine and use of an average relative shift. Furthermore, the idea of mark measurement is known from WO2014146906 A2 which is herein incorporated by reference in its entirety. WO2014146906 A2 discloses measuring marks in the resist and feeding forward the measured information to the next exposure as a substrate specific correction.

Optionally, a third mark, which is on a different layer to the first mark and the second mark, may be provided. The position of the third mark can be determined and the position may be used with the determined relative shift to control positioning of the different layer of the substrate and/or any other layer of the substrate. The third mark may be a known, standard mark, such as an alignment mark.

Figure 6:
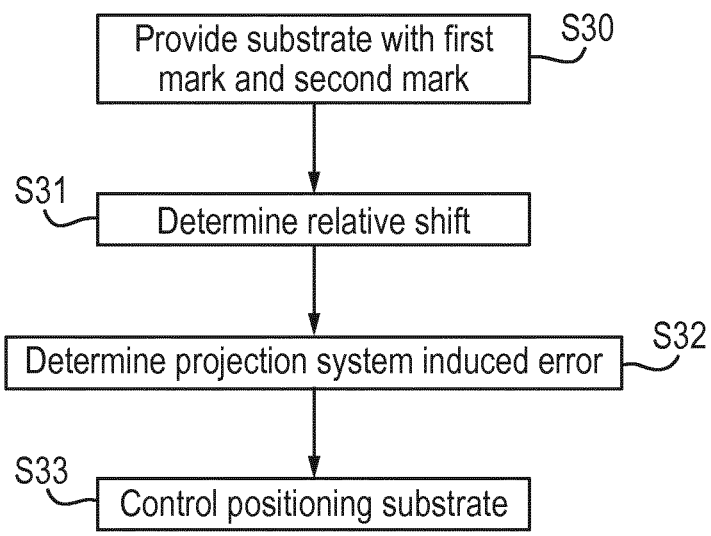
FIG. 6 is a flowchart of a method of controlling positioning of a substrate.

An example implementation for the above described method is shown in the flow chart of FIG. 6. In step S30, a substrate with a first mark and a second mark is provided. It is noted that this may include additional steps of exposing the first mark and/or the second mark as will be further described. Additionally, this step may include selecting/designing the structures used for the first mark and/or the second mark. Thus, it is possible to select a first mark and/or a second mark which will have a desired relative shift. This may be beneficial, because a specific first mark and/or second mark may be chosen to allow the relative shift to be more easily and/or more accurately determined so that a more accurate estimate of the relative shift and/or projection system induced error can be determined.

In a further step S31, the relative shift is determined. This may be done using any appropriate method. Examples include those described above, i.e. using measurements of the position of the first and the second mark, or using diffractive based measurements. Optionally, the relative shift can be used to determine a projection system induced error as shown in step S32 For example, as described above, there often exists a linear relationship between a Zernike aberration and the determined relative shift. Knowledge of the relationship allows determination of the projection system induced error (aberration) based on the determined relative shift. It is noted that more complicated relationships may be determined and used.

The determined relative shift and/or projection system induced error can then be used to control positioning of one layer of the substrate, a further layer of the substrate or a layer of a further substrate as in step S33. The determined relative shift and/or projection system induced error can optionally be used as part of a feedback or feedforward system. The determined relative shift and/or the determined projection system induced error can be used in a feedback loop to control positioning of a layer of a further substrate and/or in a feedforward loop to control positioning of a further layer of the same substrate. This means that the determined relative shift and/or the determined projection system induced error can be used to control positioning of other layers of the substrate or layers of further substrates and the other layers/further substrates can be exposed taking into account the projection system induced error. Step 33 includes controlling the positioning of a substrate using feedforward and/or feedback methods. After the layer has been positioned in accordance with the above, it can be exposed to radiation and the above described method should reduce or prevent errors due to projection system aberrations.

Advantageously, the feedback and feedforward loops means that the determined projection system induced error and/or the determined relative shift only needs to be determined for a single layer and/or substrate and the determined projection system induced error and/or relative shift can then be used to correct/improve positioning of further layers and/or substrates.

The projection system induced error may refer to any error due to projection system aberration. This may comprise projection system drift and/or projection system heating. For example, the projection system drift may include intrasubstrate drift granularity (i.e. from a first exposed field to a last exposed field). This may require denser measurements per substrate than would otherwise be needed. Intra-substrate correction of the projection system induced error can also be improved by careful distribution of a number of first marks and second marks provided per substrate and the number of substrates per lot, ideally in addition to a good estimation model. For example, considering an example using a substrate alignment mark, aberration impact on a substrate alignment mark may be considered as translation-X and translation-Y. A large number of points are not needed to calculate translation per substrate. Depending on intra lot drift, measurement scheme may change, as indicated below. Using this method can avoid undesirable increases in the measurement time.

The relative shift and/or the projection system induced error can be determined for multiple layers and/or substrates. For example, all substrates in the lot can be measured, or only a few of the substrates, which may optionally be evenly spread throughout the lot.

The second embodiment can be applied using the difference between any combination of different structures, such as overlay marks, alignment marks and product features, etc. In the example above, the first mark may be an alignment mark. However, the first mark may alternatively be an overlay mark. The second mark may be a product feature or a feature having a similar response to the projection system induced error as a product feature. In other words, the second mark may be any structure which is affected by an aberration in the projection system in the same or a similar way as a product feature would be affected. The structure used for the second mark does not have to be an actual product feature. It will be understood that the first and second terminology used in relation to the marks is simply used for the purposes of distinguishing between the different marks. Thus, the first mark could be replaced with the second mark and vice versa. The first mark and/or the second mark and/or the first mark overlapped with the second mark may have the same overall dimension of known overlay marks. The first mark and/or the second mark may have the pitch of known marks, such as known alignment marks, and may be measurable using known measurement systems.

Using different types of mark mean that aberration related drifts and the offsets between these marks can be corrected. If the static projection system aberration exists, the methods of the present embodiment can measure this static offset using an alignment mark the first mark and another structure, such as an overlay mark or a product mark as the second mark. The static non-zero offsets can be minimized using the above described methods such that non-zero offsets will not need to be calibrated. Different types of mark, such as alignment marks, overlay marks and product features or the like may have different pitches. Therefore, it may be difficult of impossible to match the different types of mark such that they overlap but do not touch. In the present embodiment, the methods described above should allow for this using measurements and corrections for the differences in pitch.

One of the advantages of the present embodiment is that dense sampling is not required to obtain the necessary relative shift described above. Therefore, the measurements can be carried out using systems already in place as described above, i.e. metrology systems which are already integrated in the litho tool 100. Furthermore, this means that it is not necessary to have a large number of marks. The layer comprising the first mark may comprise any number of suitable first marks. The layer comprising the second mark may comprise any number of suitable second marks. Preferably, there are the same number of first marks and second marks. For example, the layer comprising the first mark may comprises at least five to ten first marks and the layer comprising the second mark may comprise a corresponding number of second marks, i.e. the same number of second marks. In other words, there may be the same number of first marks and second marks on the relevant layers. The projection system induced error is generally a translation error in case of standard inter field wafer alignment whose layout is one mark per field with many fields, which means that a small number of marks, e.g. five to ten, may be sufficient. Furthermore, linear and higher order parameter errors can be taken into account by using additional marks in a field. Thus, there can be more than ten first marks and more than ten second marks on the relevant layer(s).

The methods described in the second embodiment may be used to determine the relative shift and/or the projection system induced error as described above. As already indicated, the projection system induced error can be an issue when any marks are created on the layer of the substrate. Thus, when determining the updated position for the feature using the methods of the first embodiment, determining the updated position for the feature may use the relative shift and/or the projection system induced error determined in the methods described in relation to the second embodiment.

In a regular second-to-first layer overlay measurement there is a bottom grating which is printed during the first layer exposure, and there is a top grating which is printed during the second layer exposure. In the second embodiment described above, the first mark and the second mark are provided on one layer. The one layer may be the first layer. This means that the relative responses of different pattern structures due to projection system heating can be measured after they are printed (i.e. exposed).

In the second embodiment, there is provided a further method for controlling positioning of a substrate. The further method may have all of the same features as described in the second embodiment and comprises providing a substrate with a first mark on a first layer and a second mark on a second layer of the substrate. In the further method, the second mark is the equivalent of the first mark and the second mark described above. Thus, in the further method, the second mark comprises at least two types of feature. Thus, the second mark comprises at least one first portion and at least one second portion as described above. In the further method, the at least one first portion corresponds to the first mark described above and the at least one second portion corresponds to the second mark described above, and the first mark of the further method corresponds to an additional mark (i.e. the third mark in the context of the method already described). The further method may further comprise determining the position of the first mark and determining a relative shift of the at least one first portion with respect to the at least one second portion. The method comprises controlling positioning of the first layer or a further layer of the substrate or any layer on a further substrate based on the determined position and a determined relative shift. The further method differs from the previously described method due to the inclusion of the first mark (which corresponds to the third mark in the method described above). Furthermore, there may be different numbers of first mark and second mark in the further method.

Using this further method, the positioning of the first layer or a further layer of the substrate or any layer on a further substrate can be controlled based on the position of the first mark and the relative shift of the at least one first portion with respect to the at least one second portion. The relative shift of the at least one first portion with respect to the at least one second portion can be described as a characteristic of the second mark. Similarly to the method described above, the relative shift of the at least one first portion with respect to the at least one second portion can be used to determine a projection system induced error and the projection system induced error can be used to control positioning of the first layer or a further layer of the substrate or any layer on a further substrate. The relative shift of the at least one first portion with respect to the at least one second portion can be determined in the same way as described above with respect to the first mark and the second mark above, i.e. using position measurements and/or diffraction based measurements.

In the second embodiment, a substrate is provided with the first mark and the second mark on the relevant layers. For example the first mark is provided to a first layer and the second marker is provided to a second layer on the substrate. However, the method may further comprise a step of exposing the first mark and/or the second mark on the respective layers of the substrate. This step is not necessary within the context of the invention because a substrate already comprising these marks can be provided but the first mark and/or the second mark can be made on the relevant layers of the substrate using the lithographic tool 100 described above.

The present embodiment described in the above method and further method provides many advantages. For example, using the projection system induced error as described above may reduce overlay error and thus improve yield of the lithographic process. As described, static or dynamic offsets between a substrate alignment mark and product cell may be reduced or removed. As described, using the method of the second embodiment, the determined marker position may be corrected by the determined relative shift (which is based on measurements purely in resist; eg before processing takes place). As previously mentioned, etching and other processing may degrade the printed marker. Thus, no mark asymmetry is expected and measurement before such processing steps may be more accurate. Therefore the accuracy and precision may be higher than measuring etched mark with mark asymmetry. The methods of the second embodiment will improve the correction which can be applied for each substrate for a known drift using substrate level control. This means that the correction (for the projection system induced error) may be substrate specific; eg a relative shift may be measured for substrate A and a correction may be determined and applied specifically for a next layer on the same substrate A; hence corrections are finer than just lot based corrections which typically apply to 25 substrates at once.

The present embodiment relaxes the substrate alignment mark design rules to optimize aberration sensitivity. Thus, it is not necessary to use expensive experimental determination of sensitivities for mark design because this can be avoided. Additionally, there is more freedom to choose active alignment marks because the projection system induced error can be accounted for, thus, there is no need (or a reduced need) to consider aberration sensitivity when selecting an alignment mark. Furthermore, no additional (e.g. alignment) marker measurements are needed in order to correct for projection system induced errors. The first mark and the second mark can be measured prior to the top layer exposure, e.g. just after resist development (this is bottom layer exposure) and thus the relative shift can be determined. During the top layer exposure, there may be additional substrate alignment measurements (only standard substrate alignment). Thus, the stored relative shift can be fed back per wafer to the top layer exposure. Hence there is no throughput impact during the exposure and also the relative shift is collected at the top layer exposure.

In an embodiment, a system is provided comprising a processor configured to determine a position of a feature referenced to a substrate and/or control positioning of a substrate. The processor is configured to carry out the method according to any one of the embodiments above. The processor may be part of, or connected to, either the automated process control (APC) system and/or the supervisory control system.

The processor may be configured to: measure a position of the feature, wherein the feature is configured to enable positioning of the substrate; receive an intended placement of the feature; determine an estimate of a placement error, wherein the placement error is the difference between the intended placement and an actual placement of the feature, based on knowledge of a relative position of a first feature referenced to a first layer with respect to a second feature referenced to a second layer, wherein the first layer and the second layer are on a substrate; and determine an updated position for the feature using the estimate of the placement error and the measured position of the feature.

The processor may be configured to determine a relative shift of a first mark with respect to a second mark, wherein the first mark and the second mark are on one layer of a substrate, wherein the first mark is different from the second mark; and control positioning of a further layer of the substrate or a layer of a further substrate based on the relative shift.

The processor may be configured to provide a substrate with a first mark on a first layer and a second mark on a second layer of the substrate, the second mark comprising at least one first portion and at least one second portion; determine the position of the first mark; determine a relative shift of the at least one first portion with respect to the at least one second portion; and use the determined position and determined relative shift to control positioning of the first layer or a further layer of the substrate or any layer on a further substrate.

The above methods may be implemented using a computer program containing one or more sequences of machine-readable instructions describing methods of combining process model values and measurement values as described above. There may also be provided a data storage medium (e.g., semiconductor memory, magnetic or optical disk) having such a computer program stored therein.

In an embodiment, a program is provided for controlling determining a position of a feature referenced to a substrate and/or controlling positioning of a substrate. The program may comprise instructions for carrying out the steps of any of the methods described above.

The program may comprise instructions for carrying out the steps of: measuring a position of the feature, wherein the feature is configured to enable positioning of the substrate; receiving an intended placement of the feature; determining an estimate of a placement error, wherein the placement error is the difference between the intended placement and an actual placement of the feature, based on knowledge of a relative position of a first feature referenced to a first layer with respect to a second feature referenced to a second layer, wherein the first layer and the second layer are on a substrate; and determining an updated position for the feature using the estimate of the placement error and the measured position of the feature.

The program may comprise instructions for carrying out the steps of: determining a relative shift of a first mark with respect to a second mark, wherein the first mark and the second mark are on one layer of a substrate, wherein the first mark is different from the second mark; and controlling positioning of a further layer of the substrate or a layer of a further substrate based on the relative shift.

The program may comprise instructions for carrying out the steps of: providing a substrate with a first mark on a first layer and a second mark on a second layer of the substrate, the second mark comprising at least one first portion and at least one second portion; determining the position of the first mark; determining a relative shift of the at least one first portion with respect to the at least one second portion; and using the determined position and determined relative shift to control positioning of the first layer or a further layer of the substrate or any layer on a further substrate. The computer program may be executed for example within the control unit LACU of FIG. 1, or some other controller, for example within a metrology system that includes the metrology apparatus 140, or in an advanced process control system or separate advisory tool. The program may optionally be stored in a memory which is part of or can be accessed by the automated process control (APC) system and/or the supervisory control system.

Further embodiments of the invention are disclosed in the list of numbered embodiments below:

1. A method for determining a position of a feature referenced to a substrate, the method comprising:
   measuring a position of the feature, wherein the feature is configured to enable positioning of the substrate;
   receiving an intended placement of the feature;
   determining an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and
   determining an updated position for the feature using the estimate of the placement error and the measured position of the feature.
2. The method of embodiment 1, further comprising positioning a substrate on the basis of the updated position of the feature.
3. The method of embodiment 2 further comprising a step of exposing the substrate to a radiation beam.
4. The method of embodiment 2 or 3, wherein the method is carried out using a lithographic apparatus.
5. The method of any of the preceding embodiments, wherein the feature is on the first layer or on the second layer.
6. The method of any of the preceding embodiments, wherein the feature is on a layer of a substrate having the first layer and the second layer, and the feature is on a different layer than the first layer and the second layer.
7. The method of any of the preceding embodiments, wherein the position of the feature is measured on a substrate different from the substrate associated with the determined estimate of the placement error.
8. The method of any of the preceding embodiments, wherein the method further comprises measuring the position of a first reference feature relative to the position of a second reference feature to determine an overlay error and using the overlay error to determine the estimate of the placement error.
9. The method of any of the preceding embodiments, wherein the method further comprises modelling an overlay error between the first layer and the second layer to determine the position of the first reference feature relative to the position of the second reference feature.
10. The method of embodiment 9, further comprising receiving context information and/or lithographic apparatus information, and using the context information and/or lithographic apparatus information to model the overlay error, wherein the context information and/or lithographic apparatus relates to measured and/or modelled deformation of at least one of the substrate, a patterning device and/or a projection system.

11. The method of embodiment 9 or 10, wherein modelling the overlay error comprises using a predetermined value based on overlay data.

12. The method of any one of embodiments 8 to 11, wherein the estimate of the placement error is determined to be the same as the overlay error.

13. The method of any one of the preceding embodiments, wherein the feature is a grating and/or an alignment mark.

14. A system comprising a processor configured to determine a position of a feature referenced to a substrate, the processor being configured to:
measure a position of the feature, wherein the feature is configured to enable positioning of the substrate;
receive an intended placement of the feature;
determine an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and
determine an updated position for the feature using the estimate of the placement error and the measured position of the feature.

15. A program for controlling determining a position of a feature referenced to a substrate, the program comprising instructions for carrying out the steps of:
measuring a position of the feature, wherein the feature is configured to enable positioning of the substrate;
receiving an intended placement of the feature;
determining an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and
determining an updated position for the feature using the estimate of the placement error and the measured position of the feature.

16. A method for controlling positioning of a substrate, comprising:
providing a substrate with a first mark and a second mark on one layer of the substrate, wherein the first mark is different from the second mark;
determining a relative shift of the first mark with respect to the second mark; and
controlling positioning of the one layer of the substrate, a further layer of the substrate or a layer of a further substrate based on the determined relative shift.

17. The method of embodiment 16, wherein the first mark and the second mark have different sensitivities to an aberration in a projection system, wherein the projection system is used to expose the first mark and the second mark on the substrate.

18. The method of embodiment 16 or 17, further comprising determining a projection system induced error using the determined relative shift and the controlling positioning of the one layer of the substrate, a further layer of the substrate or a layer of a further substrate uses the determined projection system induced error.

19. The method of any one of embodiments 16-18, further comprising measuring the position of the first mark and the second mark and calculating the distance between the first mark and the second mark, and wherein the relative shift is determined using the calculated distance between the first mark and the second mark and an expected distance between the first mark and the second mark.

20. The method of any one of embodiment 16-18, wherein the relative shift is determined using a diffraction based measurement.

21. The method of any one of embodiments 16-20, wherein the determined relative shift is used in a feedback loop to control positioning of a layer of a further substrate and/or in a feedforward loop to control positioning of a further layer of the same substrate.

22. The method of any one of embodiments 16-21, wherein the first mark is an alignment mark or an overlay mark, and wherein the second mark is a product feature or a feature having a similar response to the projection system induced error as a product feature.

23. The method of any one of embodiments 16-22, wherein the layer comprising the first mark comprises at least five to ten first marks and the layer comprising the second mark comprises the same number of second marks.

24. The method of any one of embodiments 16-23, wherein the first mark and the second mark overlap.

25. The method of any one of embodiments 16-24, wherein the first mark has multiple first portions and the second mark has multiple second portions.

26. A method for controlling positioning of a substrate, comprising:
providing a substrate with a first mark on a first layer and a second mark on a second layer of the substrate, the second mark comprising at least one first portion and at least one second portion;
determining the position of the first mark;
determining a relative shift of the at least one first portion with respect to the at least one second portion; and
controlling positioning of the first layer or a further layer of the substrate or any layer on a further substrate based on the determined position and the determined relative shift.

27. The method of embodiment 26, wherein the at least one first portion and the at least one second portion have different sensitivities to an aberration in a projection system, wherein the projection system is used to expose the second mark.

28. The method of embodiment 26 or 27, wherein the relative shift is determined by measuring of a position of the at least one first portion and a position of the at least one second portion and/or using a diffraction based measurement.

29. The method of any one of embodiments 26-28, wherein the first mark has multiple first portions and the second mark has multiple second portions.

30. The method of any one of embodiments 26-29, wherein the first portions and the second portions are interlaced.

31. The method of any one of embodiments 25 to 30, wherein a first portion comprises fewer elements than a second portion.

32. The method of any one of embodiments 25-31, wherein a first portion comprises only a single element.

33. The method of any one of embodiments 25-32, wherein a single element of a first portion is larger than a single element of a second portion.

34. The method of any one of embodiments 25-33, wherein at least one of the second portions comprises a plurality of elements.

35. The method of embodiment 34, wherein the pitch between the second portions is larger than the pitch between the plurality of elements of the second portion.

36. The method of embodiment 34 or 35, wherein a single element of a first portion corresponds in size to the plurality of elements making up a second portion.

37. The method of any one of embodiments 25 and 29-36, wherein the first portions are substantially consistent in shape and pitch, and the second portions are substantially consistent in shape and pitch.

38. The method of any one of embodiments 26-36, wherein the determined position and the relative shift are used to determine a projection system induced error and the projection system induced error is used to control positioning of the first layer or a further layer of the substrate or any layer on a further substrate.

39. The method of any one of embodiments 16-25 or 37, wherein the determined projection system induced error is due to projection system drift and/or projection system heating.

40. The method of any one of embodiments 16-25, 38 or 39, wherein the determined projection system induced error is used in a feedback loop to control positioning of a layer of a further substrate and/or in a feedforward loop to control positioning of a further layer of the same substrate.

41. The method of any one of embodiments 16-40, further comprising exposing the first mark and the second mark on the respective layer of the substrate.

42. The method of any one of embodiments 1 to 13, wherein determining the updated position for the feature uses the relative shift and/or the projection system induced error determined in any one of embodiments 16 to 41.

43. A system comprising a processor configured to control positioning of a substrate, the processor being configured to:
  determine a relative shift of a first mark with respect to a second mark, wherein the first mark and the second mark are on one layer of a substrate, wherein the first mark is different from the second mark; and
  control positioning of a further layer of the substrate or a layer of a further substrate using the determined relative shift.

44. A program for controlling positioning of a substrate, the program comprising instructions for carrying out the steps of:
  determining a relative shift of a first mark with respect to a second mark, wherein the first mark and the second mark are on one layer of a substrate, wherein the first mark is different from the second mark; and
  controlling positioning of a further layer of the substrate or a layer of a further substrate using the determined relative shift.

45. A system comprising a processor configured to control positioning of a substrate, the processor being configured to:
  provide a substrate with a first mark on a first layer and a second mark on a second layer of the substrate, the second mark comprising at least one first portion and at least one second portion;
  determine the position of the first mark;
  determine a relative shift of the at least one first portion with respect to the at least one second portion; and
  use the determined position and the determined relative shift to control positioning of the first layer or a further layer of the substrate or any layer on a further substrate.

46. A program for controlling positioning of a substrate, the program comprising instructions for carrying out the steps of:
  providing a substrate with a first mark on a first layer and a second mark on a second layer of the substrate, the second mark comprising at least one first portion and at least one second portion;
  determining the position of the first mark;
  determining a relative shift of the at least one first portion with respect to the at least one second portion; and
  using the determined position and the determined relative shift to control positioning of the first layer or a further layer of the substrate or any layer on a further substrate.

CONCLUSION

In conclusion, the present disclosure provides a method generating an updated position for a feature referenced to a substrate, which can be used in various different ways. This allows the error introduced when forming the feature to be reduced or negated by processing steps. The present disclosure also provides a method for controlling positioning of a substrate. This allows the effect of projection system induced error to be reduced or prevented.

The disclosed methods allow the provision of a lithographic apparatus and methods of operating a lithographic apparatus in which performance parameters such as overlay can be improved, without the need for additional measurements, or even with a reduced number of measurements. The determination of the first reference feature and the second reference feature can be performed with or without using additional context information and/or lithographic apparatus information. Throughput can be maintained and/or increased, due to the increased accuracy which substrates (including those for which no measurement data associated with the first reference feature and the second reference feature is available) can be positioned without the loss of performance that might otherwise result.

The steps of combining determining an estimate of the placement error and determining an updated position can be performed in any suitable processing apparatus, which may located anywhere in the facility of FIG. 1, or may be physically remote from the facility. Steps of the method may be carried out in separate parts of the apparatus.

The updated position and/or estimated position error may be calculated in the supervisory control system of FIG. 1, or in the litho tool control unit LACU. They may be calculated in a remote system and communicated to the facility afterwards. Any model and measurement data may be delivered separately to a processing apparatus which then combines them as part of calculating the estimate of the position error and/or the updated position.

The method and variations above are described as being carried out using a lithographic apparatus. However, other apparatus may be used. The patterning step of a lithographic manufacturing process is only one example where the principles of the present disclosure may be applied. Other parts of the lithographic process, and other types of manufacturing process, may also benefit from the generation of modified estimates and corrections in the manner disclosed herein.

These and other modifications and variations can be envisaged by the skilled reader from a consideration of the present disclosure. The breadth and scope of the present invention should not be limited by any of the above-described exemplary embodiments, but should be defined only in accordance with the following claims and their equivalents.

The invention claimed is:

1. A method for determining a position of a feature referenced to a substrate, the method comprising:
   obtaining a measured position of the feature;
   receiving an intended placement of the feature;
   determining an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and
   determining an updated position for the feature using the estimate of the placement error and the measured position of the feature.

2. The method of claim 1, further comprising controlling positioning of a substrate on the basis of the updated position of the feature.

3. The method of claim 2, further comprising exposing the substrate to a radiation beam.

4. The method of claim 2, wherein the method is carried out using a lithographic apparatus.

5. The method of claim 1, wherein the feature is on a layer of a substrate having the first layer and the second layer, and the feature is on a different layer than the first layer and the second layer.

6. The method of claim 1, wherein the position of the feature is measured on a substrate different from the substrate associated with the determined estimate of the placement error.

7. The method of claim 1, further comprising measuring the position of a first reference feature relative to the position of a second reference feature to determine an overlay error and using the overlay error to determine the estimate of the placement error.

8. The method of claim 7, wherein the estimate of the placement error is determined to be the same as the overlay error or a function of the overlay error.

9. The method of claim 1, further comprising modelling an overlay error between the first layer and the second layer to determine the position of the first reference feature relative to the position of the second reference feature.

10. The method of claim 9, further comprising receiving context information and/or lithographic apparatus information, and using the context information and/or lithographic apparatus information to model the overlay error, wherein the context information and/or lithographic apparatus information relates to measured and/or modelled deformation of one or more selected from: the substrate, a patterning device and/or a projection system.

11. The method of claim 9, wherein modelling the overlay error comprises using a predetermined value based on overlay data.

12. The method of claim 1, wherein the feature is a grating and/or an alignment mark.

13. The method of claim 1, wherein the feature is on the first layer or on the second layer.

14. A system comprising a processor configured to determine a position of a feature referenced to a substrate, the processor configured to at least:
   obtain a measured position of the feature;
   receive an intended placement of the feature;
   determine an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and
   determine an updated position for the feature using the estimate of the placement error and the measured position of the feature.

15. A computer program product comprising a non-transitory computer-readable medium having instructions therein, the instruction, upon execution by a computer system, configured to cause the computer system to at least:
   obtain a measured position of a feature referenced to a substrate;
   obtain an intended placement of the feature;
   determine an estimate of a placement error, wherein the placement error is the difference between the intended placement and an actual placement of the feature, based on knowledge of a relative position of a first reference feature referenced to a first layer with respect to a second reference feature referenced to a second layer, wherein the first layer and the second layer are on a substrate; and
   determine an updated position for the feature using the estimate of the placement error and the measured position of the feature.

16. The computer program product of claim 15, wherein the instructions are further configured to cause the computer system to cause control of positioning of a substrate on the basis of the updated position of the feature.

17. The computer program product of claim 15, wherein the feature is on a layer of a substrate having the first layer and the second layer, and the feature is on a different layer than the first layer and the second layer.

18. The computer program product of claim 15, wherein the position of the feature is measured on a substrate different from the substrate associated with the determined estimate of the placement error.

19. The computer program product of claim 15, wherein the instructions are further configured to cause the computer system to obtain a measured position of a first reference feature relative to the position of a second reference feature to determine an overlay error and use the overlay error to determine the estimate of the placement error.

20. The computer program product of claim 15, wherein the instructions are further configured to cause the computer system to model an overlay error between the first layer and the second layer to determine the position of the first reference feature relative to the position of the second reference feature.

* * * * *